United States Patent [19]

Hirai et al.

[11] Patent Number: 4,499,172
[45] Date of Patent: Feb. 12, 1985

[54] HEAT-DEVELOPABLE COLOR LIGHT-SENSITIVE MATERIAL WITH ALKYL CARBOXYLIC ACID BASE PRECURSOR CONTAINING TRIPLE BOND

[75] Inventors: Hiroyuki Hirai; Kozo Sato, both of Kanagawa, Japan

[73] Assignee: Fuji Photo Film Co., Ltd., Kanagawa, Japan

[21] Appl. No.: 595,149

[22] Filed: Mar. 30, 1984

[30] Foreign Application Priority Data

Mar. 31, 1983 [JP] Japan ................................. 58-55693

[51] Int. Cl.$^3$ ......................... G03C 1/40; G03C 5/54; G03C 1/06
[52] U.S. Cl. .................................. 430/203; 430/351; 430/559; 430/619; 430/955
[58] Field of Search ............... 430/203, 351, 353, 617, 430/619, 559, 955, 151

[56] References Cited

U.S. PATENT DOCUMENTS 3,220,846 11/1965 Tinker et al. ........................ 430/619
4,463,079 7/1984 Naito et al. ......................... 430/203

*Primary Examiner*—Richard L. Schilling
*Attorney, Agent, or Firm*—Sughrue, Mion, Zinn, Macpeak and Seas

[57] ABSTRACT

A heat-developable color light-sensitive material comprising a support having thereon at least a light-sensitive silver halide, a binder, a dye releasing redox compound which is capable of reducing the light-sensitive silver halide and is capable of reacting with the light-sensitive silver halide by heating to release a hydrophilic dye and a salt of an alkylcarboxylic acid having a triple bond between the α-position carbon atom and the β-position carbon atom with an organic base as a base precursor.

The heat-developable color light-sensitive material containing the novel base precursor has good stability during preservation and provides a color image having a high color density and low fog in a short time by a simple procedure. A method of forming a color image using the heat-developable color light-sensitive material is also disclosed.

14 Claims, No Drawings

HEAT-DEVELOPABLE COLOR LIGHT-SENSITIVE MATERIAL WITH ALKYL CARBOXYLIC ACID BASE PRECURSOR CONTAINING TRIPLE BOND

FIELD OF THE INVENTION

The present invention relates to a novel light-sensitive material containing a dye releasing redox compound capable of reacting with a light-sensitive silver halide by heating under a substantially water free condition to release a hydrophilic dye. Particularly, the present invention relates to a heat-developable color light-sensitive material containing a specific base precursor described hereinafter. The term "base precursor" used herein means a substance which releases a basic component upon heat-decomposition.

BACKGROUND OF THE INVENTION

Photographic processes using silver halide have been most widely used in the past due to their excellent photographic properties such as sensitivity or control of gradation, etc., as compared with other photographic processes, such as an electrophotographic process or a diazo photographic process. In recent years, with respect to image formation processes for light-sensitive materials using silver halide, many techniques capable of easily and quickly obtaining images have been developed by changing the conventional wet process using a developing solution into a dye development process such as a process using heat, etc.

Heat-developable light-sensitive materials are known in the field of these techniques. Heat-developable light-sensitive materials and processes therefor have been described, for example, in Shashin Kogaku no Kiso (The Foundation of Photographic Technology), pages 553 to 555 (published by Corona Co., 1979), Eizo Jyoho (The Image Information), page 40 (April, 1978), Nebletts Handbook of Photography and Reprography, 7th Ed., pages 32 to 33 (Van Nostrand Reinhold Company), U.S. Pat. Nos. 3,152,904, 3,301,678, 3,392,020 and 3,457,075, British Pat. Nos. 1,131,108 and 1,167,777, and Research Disclosure, No. 17029, pages 9 to 15 (June, 1978).

Many different dry processes for obtaining color images have been proposed. With respect to processes for forming color images by the reaction of an oxidation product of a developing agent with a coupler, it has been proposed to use a p-phenylenediamine type reducing agent and a phenolic coupler or an active methylene coupler as described in U.S. Pat. No. 3,531,286, a p-aminophenol type reducing agent as described in U.S. Pat. No. 3,761,270, a sulfonamidophenol type reducing agent as described in Belgian Pat. No. 802,519 and Research Disclosure, pages 31 and 32 (September, 1975) and the combination of a sulfonamidophenol type reducing agent and a 4-equivalent coupler as described in U.S. Pat. No. 4,021,240. These processes, however, are disadvantageous in that turbid color images are formed, because a reduced silver image and a color image are simultaneously formed on the exposed area after heat-development. In order to eliminate these disadvantages, there have been proposed a process which comprises removing a silver image by liquid processing or a process which comprises transferring only the dye to another layer, for example, a sheet having an image receiving layer. However, the latter process is not desirable because it is not easy to transfer only the dye as distinguishable from unreacted substances.

Another process which comprises introducing a nitrogen containing heterocyclic group into a dye, forming a silver salt and releasing a dye by heat-development has been described in Research Disclosure, No. 16966, pages 54 to 58 (May, 1978). According to this process, clear images cannot be obtained, because it is difficult to control the release of dyes from nonexposed areas, and thus it is not a conventionally applicable process.

Also, processes for forming a positive color image by a heat-sensitive silver dye bleach process, with useful dyes and methods for bleaching have been described, for example, in Research Disclosure, No. 14433, pages 30 to 32 (April, 1976), ibid., No. 15227, pages 14 and 15 (December, 1976) and U.S. Pat. No. 4,235,957.

However, this process requires an additional step and an additional material for accelerating bleaching of dyes, for example, heating with a superposed sheet with an activating agent. Furthermore, it is not desirable because the resulting color images are gradually reduced and bleached by coexisting free silver during long periods of preservation.

Moreover, a process for forming a color image utilizing a leuco dye has been described, for example, in U.S. Pat. Nos. 3,985,565 and 4,022,617. However, this process is not desirable because it is difficult to stably incorporate the leuco dye in the photographic material and coloration gradually occurs during preservation.

SUMMARY OF THE INVENTION

The present invention provides a novel color light-sensitive material which forms a dye image by heating under a condition substantially free from water, eliminating the drawbacks present in known materials.

Therefore, an object of the present invention is to provide a heat-developable color light-sensitive material which forms a color image having a high density in a short time.

Another object of the present invention is to provide a light-sensitive material containing a novel base precursor which forms a color image having a high density and low fog.

Still another object of the present invention is to provide a heat-developable color light-sensitive material having a good stability during preservation. The term "stable during preservation" used herein means that change in photographic properties such as maximum density, minimum density, sensitivity, etc., is small during preservation of the light-sensitive material prior to heat-development.

These and other objects of the present invention will become more apparent from the following detailed description and examples.

These objects of the present invention are accomplished with a heat-developable color light-sensitive material comprising a support having thereon at least a light-sensitive silver halide, a binder, a dye releasing redox compound which is capable of reducing the light-sensitive silver halide and is capable of reacting with the light-sensitive silver halide by heating to release a hydrophilic dye and a salt of an alkylcarboxylic acid having a triple bond between the $\alpha$-position carbon atom and the $\beta$-position carbon atom with an organic base as a base precursor.

DETAILED DESCRIPTION OF THE INVENTION

Preferred compounds of the base precursors used in the present invention, that is, the salt of an alkylcarboxylic acid having a triple bond between the α-position carbon atom and the β-position carbon atom with an organic base, are represented by the following general formula (I) or (II):

(R—C≡C—CO$_2$H)$_x$.B      (I)

R(—C≡C—CO$_2$H)$_2$.B$_y$      (II)

wherein R represents a monovalent residue selected from a hydrogen atom, an alkyl group, a substituted alkyl group, a cycloalkyl group, an alkenyl group, an alkynyl group, an aryl group, a substituted aryl group, a heterocyclic group, a substituted heterocyclic group, an aralkyl group, a substituted aralkyl group, an acyl group, an alkoxycarbonyl group, a carbamoyl group, a substituted carbamoyl group, —CO$_2$M (wherein M represents an alkali metal) and —CO$_2$H.B or a divalent residue selected from an alkylene group, an arylene group and a heterocyclic divalent residue and these groups may be further substituted; B represents an organic base; x represents 1 when B represents a monoacidic base or 2 when B represents a diacidic base; and y represents 1 when B represents a diacidic base or 2 when B represents a monoacidic base.

Examples of substituents in the substituted alkyl groups include an aryl group, an alkyl group, an alkoxy group, an alkoxycarbonyl group, an acyl group, an acylamino group, a carbamoyl group, a dialkylcarbamoyl group, a sulfamoyl group, a dialkylsulfamoyl group, an alkylsulfonyl group, an arylsulfonyl group, a cyano group, a nitro group, a trifluoromethyl group and a halogen atom. These substituents also correspond to those in the substituted aryl group, the substituted heterocyclic group, the substituted aralkyl group and the substituted carbamoyl group.

Suitable examples of R include a hydrogen atom, an alkyl group having from 1 to 5 carbon atoms, a substituted alkyl group having from 1 to 5 carbon atoms, a cycloalkyl group having from 5 to 8 carbon atoms, an alkenyl group having from 2 to 5 carbon atoms, an alkynyl group having from 2 to 5 carbon atoms, a phenyl group, a substituted phenyl group (substituents are, for example, a halogen atom, a methoxy group, a cyano group, a nitro group, etc.), a naphthyl group, a substituted naphthyl group (substituents are, for example, a methoxy group, etc.), an anthryl group, a pyridyl group, a substituted pyridyl group, a thienyl group, a substituted thienyl group, a thiazolyl group, a benzoxazolyl group, a benzothiazolyl group, an imidazolyl group, a benzimidazolyl group, a quinolyl group, a furyl group, a pyrrolyl group, an aralkyl group having from 7 to 10 carbon atoms, an acyl group having from 2 to 12 carbon atoms, an alkoxycarbonyl group having from 2 to 9 carbon atoms, a carbamoyl group, a substituted carbamoyl group having from 2 to 9 carbon atoms, —CO$_2$Na, —CO$_2$K, —CO$_2$Cs, —CO$_2$H.B (wherein B represents a base component as described above), a 1,3-phenylene group, a 1,4-phenylene group, a 1,5-naphthylene group, a 2,5-thienylene group, a 9,10-anthrylene group, etc.

It is desired that R has an appropriate electron withdrawing property for the base precursor according to the present invention to have sufficient decomposition speed. For this purpose, an alkenyl group, an alkynyl group, a phenyl group, a substituted phenyl group, a naphthyl group, a substituted naphthyl group, an anthryl group, a pyridyl group, a substituted pyridyl group, a thienyl group, a substituted thienyl group, a benzoxazolyl group, a benzothiazolyl group, an acyl group, an alkoxycarbonyl group, a carbamoyl group, a substituted carbamoyl group, —CO$_2$M, —CO$_2$H.B, a phenylene group, a naphthylene group, a thienylene group and an anthrylene group, etc., are preferably used.

Considering availability of raw materials and ease in synthesis, etc., compounds represented by the general formula (III) or (IV) described below are most preferably used:

(Ar—C≡C—CO$_2$H)$_x$.B      (III)

Ar(—C≡C—CO$_2$H)$_2$.B$_y$      (IV)

wherein Ar represents a phenyl group, a substituted phenyl group, a naphthyl group, a substituted naphthyl group, an anthryl group, a pyridyl group, a substituted pyridyl group, a thienyl group, a substituted thienyl group or a divalent group selected from these groups; and B, x and y each has the same meaning as defined above.

Of the organic bases represented by B, those having pKa of 9 or more and a boiling point of 100° C. or higher are preferred and those having pKa of 10 or more and being substantially nonvolatile at an ambient temperature and free from a bad smell are particularly preferred. Examples of particularly preferred organic bases include guanidines, cyclic guanidines, amidines, cyclic amidines, etc. Further, the organic base B has desirably a hydrophilic property and those having 10 or less of the total number of carbon atoms are preferably used. In the following, preferred examples of the organic base B are set forth.

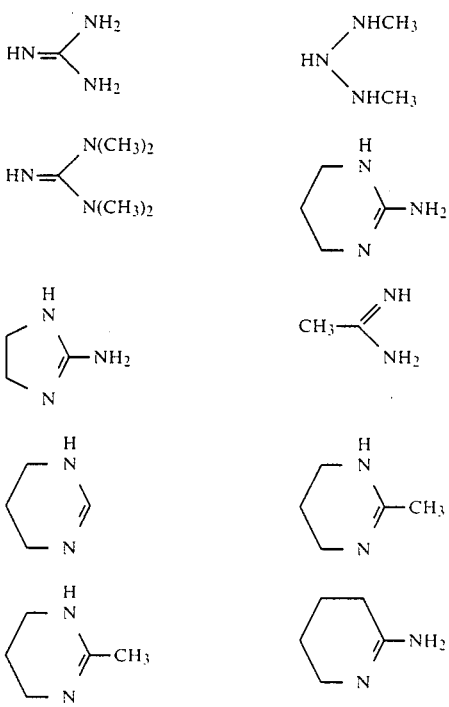

-continued

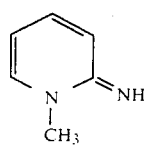 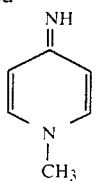

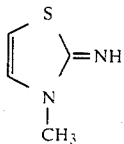 

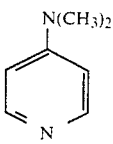 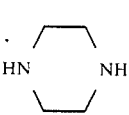

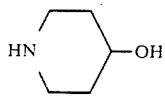 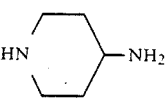

 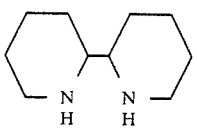

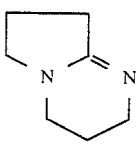 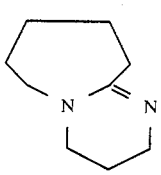

 

The base precursor used in the present invention is characterized by its structure in that the acid part is a propiolic acid derivative having a triple bond at the α-position to the carboxy group. By this structural characteristic the carboxy group is very easily subjected to decarboxylation. However, the propiolic acid derivative is extremely stable at an ambient temperature and does not release a base component until upon decarboxylation by means of heating. As the result, it is possible to fulfill two properties required to base precursors, i.e., stability during preservation at an ambient temperature and rapid decomposition (release of base) at development process.

Specific examples of the base precursors used in the present invention are set forth below, but the present invention is not to be construed as being limited thereto.

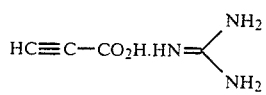 (1)

-continued

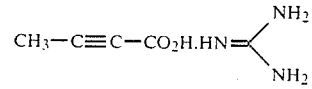 (2)

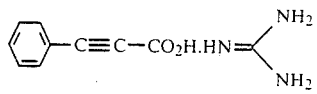 (3)

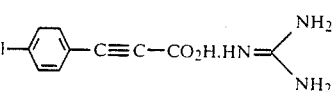 (4)

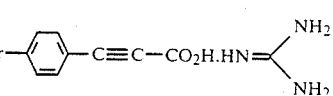 (5)

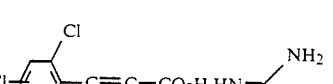 (6)

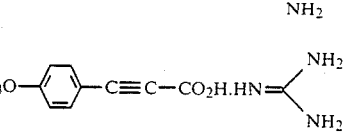 (7)

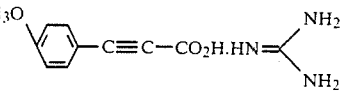 (8)

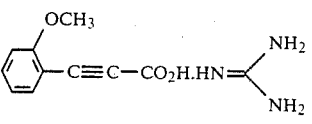 (9)

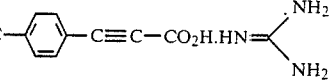 (10)

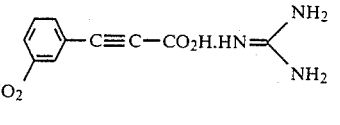 (11)

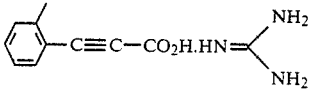 (12)

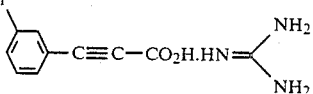 (13)

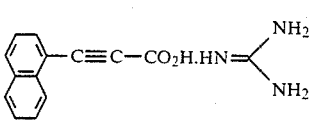 (14)

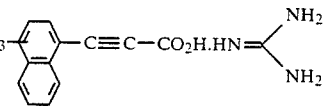 (15)

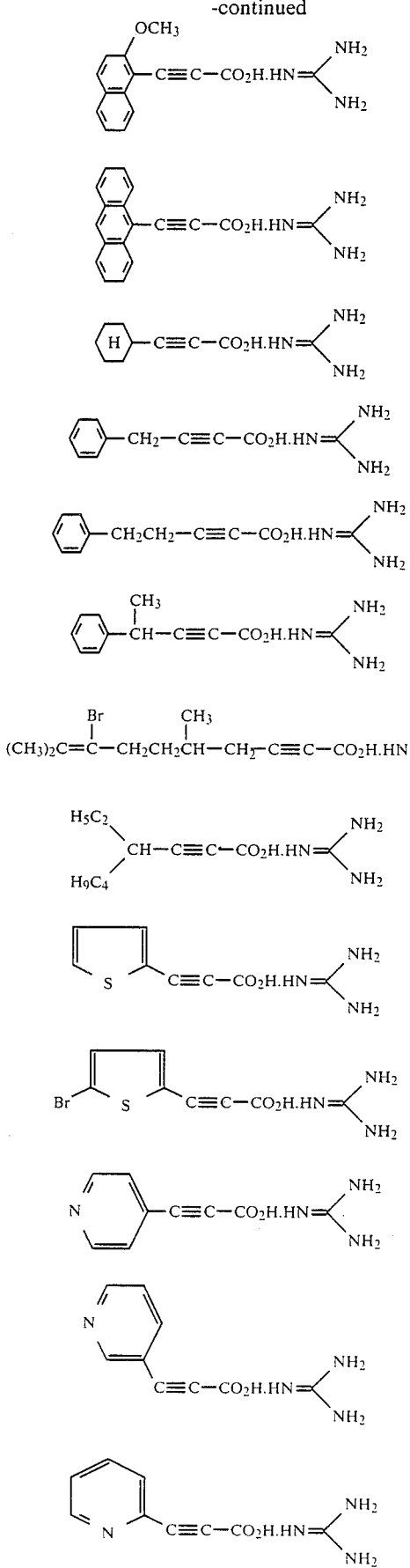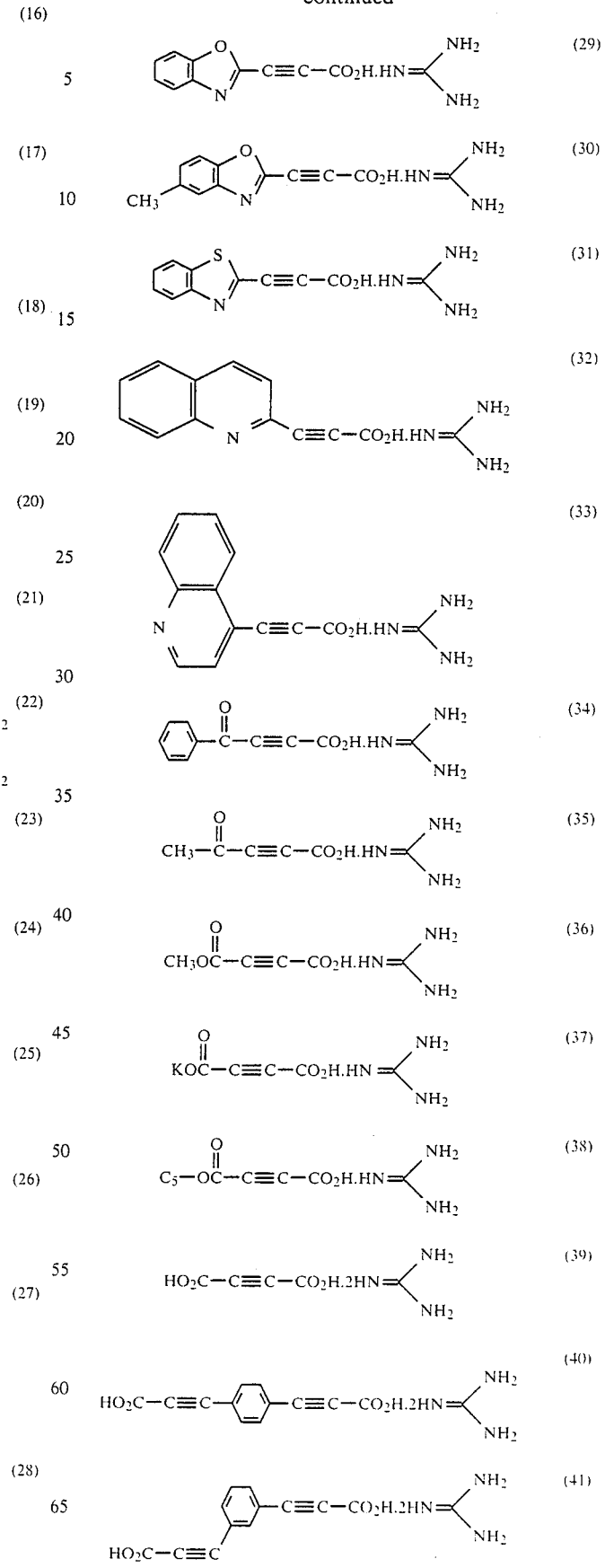

-continued

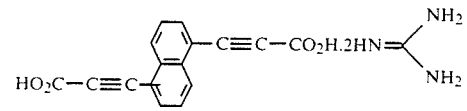 (42)

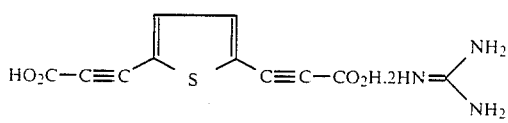 (43)

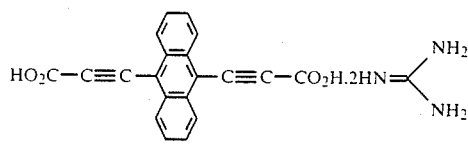 (44)

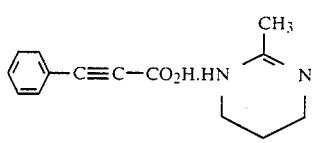 (45)

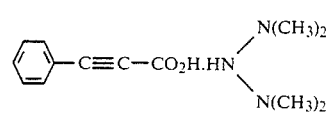 (46)

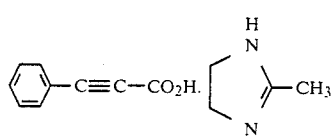 (47)

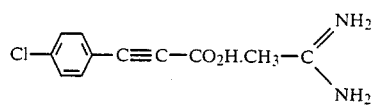 (48)

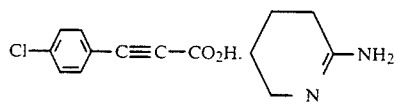 (49)

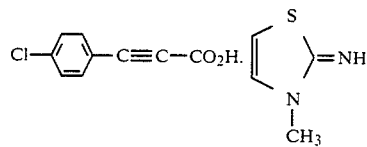 (50)

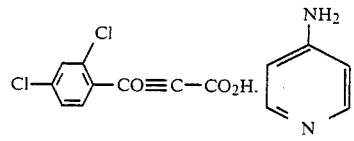 (51)

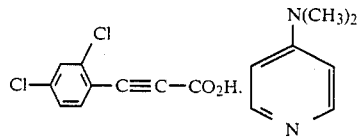 (52)

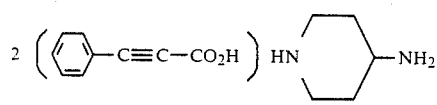 (53)

-continued

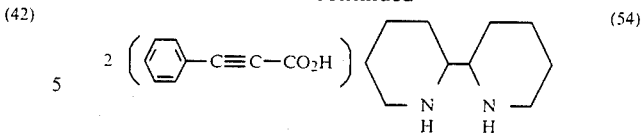 (54)

Methods for synthesizing the base precursor according to the present invention will be explained below.

The base precursor used in the present invention can be synthesized in the manner as illustrated in the following reaction scheme.

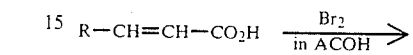

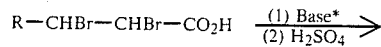

$$R-C\equiv C-CO_2H \xrightarrow{B^{**}} R-C\equiv C-CO_2H \cdot B$$

*KOH/CH₃OH, diazabicycloundecene, etc.
**The organic base as defined before.

That is, a method in which bromine is added to an acrylic acid derivative and then the brominated compound is subjected to dehydrobromination with a strong base to obtain a propiolic acid derivative. In the following, synthesis examples of the specific compounds used are set forth.

SYNTHESIS EXAMPLE 1

Synthesis of Base Precursor (3)

29.6 g of cinnamic acid was dissolved by heating in 80 ml of acetic acid and to the solution was added dropwise 32 g of bromine. After stirring at 50° C. for 15 minutes, the reaction mixture was allowed to cool and to which was gradually added 100 ml of water. The white crystals thus formed were collected by filtration, washed with water and dried. Yield: 56 g.

56 g of potassium hydroxide was dissolved in 200 ml of methanol and to the solution was added little by little the above-described crystals. The mixture was heated with stirring on a hot water bath and the methanol was distilled off. The residue was dissolved in 200 ml of water and neutralized with diluted sulfuric acid under cooling with ice. The light yellow oil thus separated was rapidly crystallized. The crystals thus formed were collected by filtration and recrystallized from water to obtain 22 g of phenylpropiolic acid.

A mixture of 14.6 g of phenylpropiolic acid obtained above, 9.0 g of guanidine carbonate and 50 ml of methanol was stirred at room temperature for 2 hours. The methanol was distilled off under reduced pressure at below 50° C. to obtain 20.2 g of Base Precursor (3) as white crystals. Melting Point: 137° to 139° C. (decomposed).

SYNTHESIS EXAMPLE 2

Synthesis of Base Precursor (4)

A mixture of 36.5 g of p-chlorocinnamic acid and 100 ml of acetic acid was heated to 50° C. and to which was added dropwise 35 g of bromine. After stirring at 50° C. for 1 hour, the reaction mixture was allowed to cool and to which was added 100 ml of ice water. The white crystals thus formed were collected by filtration, washed with water and dried. Yield: 58 g.

34.3 g of the above-described crystals was gradually added to 200 ml of methanol containing 42 g of potassium hydroxide and the mixture was heated with stirring on a hot water bath whereby the methanol was distilled off. The solid residue was recrystallized from water to obtain white crystals of potassium p-chlorophenylpropiolate. The crystals thus obtained were dissolved in 100 ml of water and neutralized with diluted sulfuric acid. The white crystals thus formed were collected by filtration, washed with water and dried to obtain 14.1 g of p-chlorophenylpropiolic acid.

A mixture of 10.8 g of p-chlorophenylpropiolic acid obtained above, 5.4 g of guanidine carbonate and 50 ml of methanol was stirred at room temperature for 1 hour. The methanol was distilled off under reduced pressure to obtain 14 g of Base Precursor (4) as white crystals. Melting Point: 186° to 187° C. (decomposed).

The base precursor according to the present invention can be used in an amount over a broad range. It is suitably used in an amount of 50% by weight or less, and more preferably in a range from 0.01% by weight to 40% by weight, based on the coated amount of a layer to be incorporated.

The base precursor according to the present invention can be incorporated into any one layer or two or more layers of the heat-developable color light-sensitive material of the present invention.

The base precursor according to the present invention can be used individually or as a mixture of two or more thereof and also it can be used together with a known dye releasing activator described hereinafter.

The base precursor according to the present invention can be incorporated into a binder by dissolving it in an organic solvent soluble in water, for example, methanol, ethanol, acetone, dimethylformamide, etc., or a mixture solution of the above-described organic solvent and water.

The heat-developable color light-sensitive material of the present invention can simultaneously provide a silver image and a mobile dye on the part corresponding to the silver image by only heating after imagewise exposure to light. The term "heat-development" used herein means that the exposed silver halide is reacted with the dye releasing redox compound by heating under the condition substantially free from water to release a dye. That is, when the heat-developable color light-sensitive material of the present invention is imagewise exposed to light and developed by heating under the condition substantially free from water, an oxidation-reduction reaction occurs between a light-sensitive silver halide and a reducing dye releasing redox compound by means of exposed light-sensitive silver halide as a catalyst to form a silver image in the exposed area. In this step, the dye releasing redox compound is oxidized by the light-sensitive silver halide to form an oxidized compound and consequently the hydrophilic mobile dye is released. Accordingly, the silver image and the mobile dye are formed in the exposed area. The above-described reaction is accelerated when a base is present. The mobile dye thus formed is transferred to, for example, a dye fixing layer whereby a dye image is obtained. However, when the base is directly incorporated into the light-sensitive material, stability during preservation thereof is adversely affected. On the contrary, when the base precursor according to the present invention is used, the stability during preservation of the light-sensitive material can be greatly improved since the base precursor only releases a base upon development at high temperature by heating.

The above-described process illustrates a case wherein a negative type silver halide emulsion is used. When an autopositive type silver halide emulsion is used, the process is the same as the case of using the negative type silver halide emulsion except that a silver image and a mobile dye are formed in the unexposed area.

The oxidation-reduction reaction between a light-sensitive silver halide and a dye releasing redox compound and the dye releasing reaction subsequently occurred are characterized by proceeding under the dry condition substantially free from water at high temperature. The high temperature condition used herein means a temperature condition of 80° C. or higher. The dry condition substantially free from water means a condition which is equilibrium with moisture in the air and to which water is not supplied from the outside of the system. Such a condition is described in *The Theory of the Photographic Process*, 4th ed., page 374 (edited by T. H. James, Macmillan Co.). It is confirmed from the fact in which a reaction rate of a sample subjected to vacuum drying under a pressure of $10^{-3}$ mmHg for one day does not decrease that a sufficiently large reaction rate is exhibited under the dry condition substantially free from water.

The dye releasing reaction has been believed to be a reaction by means of the attack with the so-called nucleophilic reagent and is usually carried out in a liquid having a high pH value of 10 or higher. In the present invention, however, the high reaction rate can be achieved under the dry condition of high temperature and substantially free from water which is an unexpected result.

Further, the dye releasing redox compound according to the present invention can undergo an oxidation-reduction reaction with silver halide without the assistance of the so-called auxiliary developing agent. This is also an unexpected result based on previous information of what may happen at ambient temperature in a wet type of development.

The above-described reaction is particularly accelerated in the presence of an organic silver salt oxidizing agent to provide a high image density. Therefore, it is a particularly preferred embodiment in which the organic silver salt oxidizing agent is coexistent.

The dye releasing redox compound which releases a hydrophilic diffusible dye used in the present invention is a compound described in European Patent Application (OPI) No. 76,492 as a dye releasing compound and is represented by the following general formula:

$$R_a-SO_2-D$$

wherein $R_a$ represents a reducing group capable of being oxidized by the silver halide; and D represents an image forming dye portion containing a hydrophilic group.

The above-described compound is oxidized correspondingly to or reversely corresponding to latent image distributed imagewise in the silver halide and releases imagewise a mobile dye.

The detail definitions of $R_a$ and D, examples of the specific compounds and synthesis examples thereof are described in European Patent Application (OPI) No. 76,492.

As the dye releasing redox compounds used in the present invention, the compounds as described, for example, in U.S. Pat. No. 4,055,428, Japanese Patent Application (OPI) Nos. 12642/81, 16130/81, 16131/81, 650/82 and 4043/82, U.S. Pat. Nos. 3,928,312 and 4,076,529, U.S. Published patent application No. B 351,673, U.S. Pat. Nos. 4,135,929 and 4,198,235, Japanese Patent Application (OPI) No. 46730/78, U.S. Pat. Nos. 4,273,855, 4,149,892, 4,142,891 and 4,258,120, etc., are also effective in addition to the above-described compounds.

Further, the dye releasing redox compounds which release a yellow dye as described, for example, in U.S. Pat. Nos. 4,013,633, 4,156,609, 4,148,641, 4,165,987, 4,148,643, 4,183,755, 4,246,414, 4,268,625 and 4,245,023, Japanese Patent Application (OPI) Nos. 71072/81, 25737/81, 138744/80, 134849/80, 106727/77, 114930/76, etc., can be effectively used in the present invention.

The dye releasing redox compounds which release a magenta dye as described, for example, in U.S. Pat. Nos. 3,954,476, 3,932,380, 3,931,144, 3,932,381, 4,268,624 and 4,255,509, Japanese Patent Application (OPI) Nos. 73057/81, 71060/81, 134850/80, 40402/80, 36804/80, 23628/78, 106727/77, 33142/80 and 53329/80, etc., can be effectively used in the present invention.

The dye releasing redox compounds which release a cyan dye as described, for example, in U.S. Pat. Nos. 3,929,760, 4,013,635, 3,942,987, 4,273,708, 4,148,642, 4,183,754, 4,147,544, 4,165,238, 4,246,414 and 4,268,625, Japanese Patent Application (OPI) Nos. 71061/81, 47823/78, 8827/77 and 143323/78, etc., can be effectively used in the present invention.

Two or more of the dye releasing redox compounds can be used together. In these cases, two or more dye releasing redox compounds may be used together in order to represent the same color or in order to represent black color.

The dye releasing redox compounds are suitably used in a range from 10 mg/m$^2$ to 15 g/m$^2$ and preferably in a range from 20 mg/m$^2$ to 10 g/m$^2$ in a total.

The dye releasing redox compound used in the present invention can be introduced into a layer of the light-sensitive material by known methods such as a method as described in U.S. Pat. No. 2,322,027. In this case, an organic solvent having a high boiling point or an organic solvent having a low boiling point as described below can be used. For example, the dye releasing redox compound is dispersed in a hydrophilic colloid after dissolved in an organic solvent having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctylbutyl phosphate, etc.), a citric acid ester (for example, tributyl acetylcitrate, etc.), a benzoic acid ester (for example, octyl benzoate, etc.), an alkylamide (for example, diethyl laurylamide, etc.), an aliphatic acid ester (for example, dibutoxyethyl succinate, dioctyl azelate, etc.), a trimesic acid ester (for example, tributyl trimesate, etc.), etc., or an organic solvent having a boiling point of about 30° C. to 160° C., for example, a lower alkyl acetate such as ethyl acetate, butyl acetate, etc., ethyl propionate, secondary butyl alcohol, methyl isobutyl ketone, β-ethoxyethyl acetate, methyl cellosolve acetate, cyclohexanone, etc. The above-described organic solvents having a high boiling point and organic solvents having a low boiling point may be used as a mixture thereof.

Further, it is possible to use a dispersion method using a polymer as described in Japanese Patent Publication No. 39853/76 and Japanese Patent Application (OPI) No. 59943/76. Moreover, various surface active agents can be used when the dye releasing redox compound is dispersed in a hydrophilic colloid. For this purpose, the surface active agents illustrated in other part of the specification can be used.

In the present invention, if necessary, a reducing agent may be used. The reducing agent in this case is the so-called auxiliary developing agent, which is oxidized by the silver halide and/or the organic silver salt oxidizing agent to form its oxidized product having an ability to oxidize the reducing group $R_a$ in the dye releasing redox compound.

Examples of useful auxiliary developing agents include the compounds specifically described in European Patent Application (OPI) No. 76,492.

In the present invention, an amount of the reducing agent added is from 0.01 mol to 20 mols per mol of silver and more preferably from 0.1 mol to 10 mols per mol of silver.

The silver halide used in the present invention includes silver chloride, silver chlorobromide, silver chloroiodide, silver bromide, silver iodobromide, silver chloroiodobromide and silver iodide, etc.

In the embodiment of the present invention in which the organic silver salt oxidizing agent is not used together with but the silver halide is used alone, particularly preferred silver halide is silver halide partially containing a silver iodide crystal in its grain. That is, the silver halide which shows the X-ray diffraction pattern of pure silver iodide is particularly preferred.

In photographic materials a silver halide containing two or more kinds of halogen atoms can be used. Such a silver halide is present in the form of a completely mixed crystal in a conventional silver halide emulsion. For example, the grain of silver iodobromide shows X-ray diffraction pattern at a position corresponding to the mixed ratio of silver iodide crystal and silver bromide crystal but not at a position corresponding to pure silver iodide crystal and pure silver bromide crystal separately.

Particularly preferred examples of silver halide used in the present invention include silver chloroiodide, silver iodobromide, and silver chloroiodobromide each containing silver iodide crystal in its grain and showing X-ray diffraction pattern of silver iodide crystal.

The process for preparing those silver halides is explained taking the case of silver iodobromide. That is, the silver iodobromide is prepared by first adding silver nitrate solution to potassium bromide solution to form silver bromide particles and then adding potassium iodide to the mixture.

Two or more kinds of silver halides in which a particle size and/or a halogen composition are different from each other may be used in mixture.

An average particle size of the silver halide used in the present invention is preferably from 0.001 μm to 10 μm and more preferably from 0.001 μm to 5 μm.

The silver halide used in the present invention may be used as is. However, it may be chemically sensitized with a chemical sensitizing agent such as compounds or sulfur, selenium or tellurium, etc., or compounds of gold, platinum, palladium, rhodium or iridium, etc., a reducing agent such as tin halide, etc., or a combination thereof. The details thereof are described in T. H. James, *The Theory of the Photographic Process*, the Fourth Edition, Chapter 5, pages 149 to 169.

In the particularly preferred embodiment of the present invention, an organic silver salt oxidizing agent is used together. The organic silver salt oxidizing agent is a silver salt which forms a silver image by reacting with the above-described image forming substance or a reducing agent coexisting, if necessary, with the image forming substance, when it is heated to a temperature of above 80° C. and, preferably, above 100° C. in the presence of exposed silver halide. By coexisting the organic silver salt oxidizing agent, the light-sensitive material which provides higher color density can be obtained.

The silver halide used in this case is not always necessarily to have the characteristic in that the silver halide contains pure silver iodide crystal in the case of using the silver halide alone. Any silver halide which is known in the art can be used.

Examples of such organic silver salt oxidizing agents include those described in European Patent Application (OPI) No. 76,492.

A silver salt of an organic compound having a carboxy group can be used. Typical examples thereof include a silver salt of an aliphatic carboxylic acid and a silver salt of an aromatic carboxylic acid.

In addition, a silver salt of a compound containing a mercapto group or a thione group and a derivative thereof can be used.

Further, a silver salt of a compound containing an imino group can be used. Examples of these compounds include a silver salt of benzotriazole and a derivative thereof as described in Japanese Patent Publication Nos. 30270/69 and 18416/70, for example, a silver salt of benzotriazole, a silver salt of alkyl substituted benzotriazole such as a silver salt of methylbenzotriazole, etc., a silver salt of a halogen substituted benzotriazole such as a silver salt of 5-chlorobenzotriazole, etc., a silver salt of carboimidobenzotriazole such as a silver salt of butyl-carboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, a silver salt as described in *Research Disclosure*, Vol. 170, No. 17029 (June, 1978) and an organic metal salt such as copper stearate, etc., are the organic metal salt oxidizing agent capable of being used in the present invention.

Methods of preparing these silver halide and organic silver salt oxidizing agents and manners of blending them are described in *Research Disclosure*, No. 17029, Japanese Patent Application (OPI) Nos. 32928/75 and 42529/76, U.S. Pat. No. 3,700,458, and Japanese Patent Application (OPI) Nos. 13224/74 and 17216/75.

A suitable coating amount of the light-sensitive silver halide and the organic silver salt oxidizing agent employed in the present invention is in a total of from 50 mg/m$^2$ to 10 g/m$^2$ calculated as an amount of silver.

The light-sensitive silver halide and the organic silver salt oxidizing agent used in the present invention are prepared in the binder as described below. Further, the dye releasing redox compound is dispersed in the binder described below.

The binder which can be used in the present invention can be employed individually or in a combination thereof. A hydrophilic binder can be used as the binder according to the present invention. The typical hydrophilic binder is a transparent or translucent hydrophilic colloid, examples of which include a natural substance, for example, protein such as gelatin, a gelatin derivative, etc., a cellulose derivative, a polysaccharide such as starch, gum arabic, etc., and a synthetic polymer, for example, a water-soluble polyvinyl compound such as polyvinyl alcohol, polyvinyl pyrrolidone, acrylamide polymer, etc. Another example of the synthetic polymer compound is a dispersed vinyl compound in a latex form which is used for the purpose of increasing dimensional stability of a photographic material.

The silver halide used in the present invention can be spectrally sensitized with methine dye or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, can be contained in these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei may also be substituted.

As nuclei having a ketomethylene structure, 5- or 6-membered heterocyclic nuclei such as a pyrazolin-5-one nucleus, a thiohydantoin nucleus, a 2-thiooxazolidin-2,4-dione nucleus, a thiazolidin-2,4-dione nucleus, a rhodanine nucleus, a thiobarbituric acid nucleus, etc., may also be used in merocyanine dyes and complex merocyanine dyes.

These sensitizing dyes can be employed individually, and can also be employed in combination thereof. A combination of sensitizing dyes is often used, particularly for the purpose of supersensitization. Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, Japanese Patent Application (OPI) Nos. 110618/77 and 109925/77, etc.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, etc., can be present. The combinations described in U.S. Pat. Nos. 3,615,613, 3,615,641, 3,617,295 and 3,635,721 are particularly useful.

A support used in the light-sensitive material or used as the dye fixing material, if desired, according to the present invention is that which can endure at the processing temperature. As an ordinary support, not only glass, paper, metal or analogues thereto may be used, but also an acetyl cellulose film, a cellulose ester film, a polyvinyl acetal film, a polystyrene film, a polycarbonate film, a polyethylene terephthalate film, and a film related thereto or a plastic material may be used. Further, a paper support laminated with a polymer such as polyethylene, etc., can be used. The polyesters described in U.S. Pat. Nos. 3,634,089 and 3,725,070 are preferably used.

In the present invention, various kinds of known dye releasing activators can be used with the specific base precursor defined in the present invention. The dye releasing activator means a substance which accelerates the oxidation-reduction reaction between the light-sensitive silver halide and/or the organic silver salt oxidizing agent and dye releasing redox compound, or accelerates release of a dye by means of its nucleophilic action to the oxidized dye releasing redox compound in the dye releasing reaction subsequently occurred, and a base and a base precursor can be used. It is particularly advantageous to use these dye releasing activators in order to accelerate the reactions in the present invention.

Examples of preferred known bases are amines which include trialkylamines, hydroxylamines, aliphatic polyamines, N-alkyl substituted aromatic amines, N-hydroxyalkyl substituted aromatic amines and bis[p-(dialkylamino)phenyl]methanes. Further, betaine tetramethylammonium iodide and diaminobutane dihydrochloride as described in U.S. Pat. No. 2,410,644, and urea and organic compounds including amino acids such as 6-aminocaproic acid as described in U.S. Pat. No. 3,506,444 are useful. The base precursor is a substance which releases a basic component by heating. Examples of typical base precursors are described in British Pat. No. 998,949. A preferred base precursor is a salt of a carboxylic acid and an organic base, and examples of the suitable carboxylic acids include trichloroacetic acid and trifluoroacetic acid and examples of the suitable bases include guanidine, piperidine, morpholine, p-toluidine and 2-picoline, etc. Guanidine trichloroacetate as described in U.S. Pat. No. 3,220,846 is particularly preferred. Further, aldonic amides as described in Japanese Patent Application (OPI) No. 22625/75 are preferably used because they decompose at a high temperature to form bases.

The total amount of the known dye releasing activators and the specific base precursor is preferably up to 50% by weight based on the amount of a dry layer coated of the light-sensitive material.

It is advantageous to use a compound represented by the general formula described below in the heat-developable color photographic material in order to accelerate development and accelerate release of a dye.

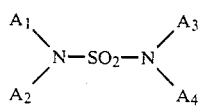

wherein $A_1$, $A_2$, $A_3$ and $A_4$, which may be the same or different, each represents a hydrogen atom or a substituent selected from an alkyl group, a substituted alkyl group, a cycloalkyl group, an aralkyl group, an aryl group, a substituted aryl group and a heterocyclic group; and $A_1$ and $A_2$ or $A_3$ and $A_4$ may combine with each other to form a ring.

The above-described compound can be used in an amount of broad range. A useful range is up to 20% by weight based on the amount of a dry layer coated of the light-sensitive material. A range of 0.1% by weight to 15% by weight is more preferred.

It is advantageous to use a water releasing compound in the present invention in order to accelerate the dye releasing reaction.

The water releasing compound means a compound which releases water by decomposition during heat development. These compounds are particularly known in the field of printing of fabrics, and $NH_4Fe(SO_4)_2 \cdot 12H_2O$, etc., as described in Japanese Patent Application (OPI) No. 88386/75 are useful.

Further, in the present invention, it is possible to use a compound which activates development and stabilizes the image at the same time. Particularly, it is preferred to use isothiuroniums including 2-hydroxyethylisothiuronium trichloroacetate as described in U.S. Pat. No. 3,301,678, bisisothiuroniums including 1,8-(3,6-dioxaoctane)bis(isothiuronium trifluoroacetate), etc., as described in U.S. Pat. No. 3,669,670, thiol compounds as described in German Patent Application (OLS) No. 2,162,714, thiazolium compounds such as 2-amino-2-thiazolium trichloroacetate, 2-amino-5-bromo-ethyl-2-thiazolium trichloroacetate, etc., as described in U.S. Pat. No. 4,012,260, compounds having α-sulfonylacetate as an acid part such as bis(2-amino-2-thiazolium)-methylene-bis(sulfonylacetate), 2-amino-2-thiazolium phenylsulfonylacetate, etc., as described in U.S. Pat. No. 4,060,420, and compounds having 2-carboxycarboxamide as an acid part as described in U.S. Pat. No. 4,088,496.

In the present invention, it is possible to use a thermal solvent. The term "thermal solvent" means a non-hydrolyzable organic material which melts at a temperature of heat treatment and melts at a lower temperature of heat treatment when it is present together with other components. Preferred examples of thermal solvents include compounds which can act as a solvent for the developing agent and compounds having a high dielectric constant which accelerate physical development of silver salts. Examples of preferred thermal solvents include those described in European Patent Application (OPI) No. 76,492.

In the present invention, though it is not always necessary to further incorporate substances or dyes for preventing irradiation or halation in the light-sensitive material, because the light-sensitive material is colored by the dye releasing redox compound, it is possible to add filter dyes or light absorbing materials, etc., into the light-sensitive material, as described in Japanese Patent Publication No. 3692/73 and U.S. Pat. Nos. 3,253,921, 2,527,583 and 2,956,879, etc., in order to further improve sharpness. It is preferred that these dyes have a thermal bleaching property. For example, dyes as described in U.S. Pat. Nos. 3,769,019, 3,745,009 and 3,615,432 are preferred.

The light-sensitive material used in the present invention may contain, if necessary, various additives known for the heat-developable light-sensitive materials and may have a layer other than the light-sensitive layer, for example, an antistatic layer, an electrically conductive layer, a protective layer, an intermediate layer, an antihalation layer, a strippable layer, etc.

The photographic emulsion layer and other hydrophilic colloid layers in the light-sensitive material of the present invention may contain various surface active agents for various purposes, for example, as coating aids, or for prevention of electrically charging, improvement of lubricating property, emulsification, prevention of adhesion, improvement of photographic properties (for example, acceleration of development, rendering hard tone or sensitization), etc.

For example, it is possible to use nonionic surface active agents such as saponin (steroid saponin), alkylene oxide derivatives (for example, polyethylene glycol, polyethylene glycol/polypropylene glycol condensates, polyethylene glycol alkyl ethers or polyethylene glycol alkylaryl ethers, polyethylene glycol esters, polyethylene glycol sorbitan esters, polyalkylene glycol alkylamines or amides, polyethylene oxide adducts of silicone, etc.), glycidol derivatives (for example, alkenylsuccinic acid polyglycerides, alkylphenol polyglycerides, etc.), polyhydric alcohol aliphatic acid esters or saccharide alkyl esters, etc.; anionic surface active agents containing acid groups such as a carboxy group, a sulfo group, a phospho group, a sulfate group, a phosphate group, etc., such as alkylcarboxylic acid salts, alkylsulfonate salts, alkylbenzenesulfonate salts, alkylnaphthalenesulfonate salts, alkyl sulfuric acid esters, alkylphosphoric acid esters, N-acyl-N-alkyltaurines, sulfosuccinic acid esters, sulfoalkyl polyoxyethylene alkylphenyl ethers, polyoxyethylene alkylphosphoric acid esters, etc.; ampholytic surface active agents such as amino acids, aminoalkylsulfonic acids, aminoalkylsulfuric acid esters or phosphoric acid esters, alkylbetaines, amine oxides, etc.; and cationic surface active agents such as alkylamine salts, aliphatic or aromatic quaternary ammonium salts, heterocyclic quaternary ammonium salts such as pyridinium salts, imidazolium salts, etc., aliphatic or heterocyclic phosphonium salts, aliphatic or heterocyclic sulfonium salts, etc.

Of the above-described surface active agents, polyethylene glycol type nonionic surface active agents having a recurring unit of ethylene oxide in their molecules may be preferably incorporated into the light-sensitive material. It is particularly preferred that the molecule contains 5 or more of the recurring units of ethylene oxide.

The nonionic surface active agents capable of satisfying the above-described conditions are well known as to their structures, properties and methods of synthesis. These nonionic surface active agents are widely used even outside this field. Representative references relating to these agents include: *Surfactant Science Series*, Vol. 1, Nonionic Surfactants (edited by Martin J. Schick, Marcel Dekker Inc., 1967), and *Surface Active Ethylene Oxide Adducts* (edited by Shoufeldt N. Pergamon Press, 1969). Among the nonionic surface active agents described in the above-mentioned references, those capable of satisfying the above-described conditions are preferably employed in connection with the present invention.

The nonionic surface active agents can be used individually or as a mixture of two or more of them.

The polyethylene glycol type nonionic surface active agents can be used in an amount of less than 100% by weight, preferably less than 50% by weight, based on a hydrophilic binder.

The light-sensitive material of the present invention may contain a cationic compound containing a pyridinium salt. Examples of the cationic compounds containing a pyridinium group used are described in PSA Journal Section B 36 (1953), U.S. Pat. Nos. 2,648,604 and 3,671,247, Japanese Patent Publication Nos. 30074/69 and 9503/69, etc.

In the photographic light-sensitive material and the dye fixing material of the present invention, the photographic emulsion layer and other binder layers may contain inorganic or organic hardeners. It is possible to use chromium salts (chromiun alum, chromium acetate, etc.), aldehydes (formaldehyde, glyoxal, glutaraldehyde, etc.), N-methylol compounds (dimethylolurea, methylol dimethylhydantoin, etc.), dioxane derivatives (2,3-dihydroxydioxane, etc.), active vinyl compounds (1,3,5-triacryloylhexahydro-s-triazine, 1,3-vinylsulfonyl-2-propanol, etc.), active halogen compounds (2,4-dichloro-6-hydroxy-s-triazine, etc.), muchohalogenic acids (mucochloric acid, mucophenoxychloric acid, etc.), etc., which are used individually or as a combination thereof.

Examples of various additives include those described in *Research Disclosure*, Vol. 170, No. 17029 (June, 1978), for example, plasticizers, dyes for improving sharpness, antihalation dyes, sensitizing dyes, matting agents, fluorescent whitening agents and fading preventing agents, etc.

If necessary, two or more layers may be coated at the same time by the method as described in U.S. Pat. No. 2,761,791 and British Pat. No. 837,095.

Various means for exposure can be used in the present invention. Latent images are obtained by imagewise exposure by radiant rays including visible rays. Generally, light sources used in this invention include tungsten lamps, mercury lamps, halogen lamps such as iodine lamps, xenon lamps, laser light sources, CRT light sources, fluorescent tubes and light-emitting diodes, etc.

In the present invention, after the heat-developable color photographic material is exposed to light, the resulting latent image can be developed by heating the whole material to a suitably elevated temperature, for example, about 80° C. to about 250° C. for about 0.5 second to about 300 seconds. A higher temperature or lower temperature can be utilized to prolong or shorten the heating time, if it is within the above-described temperature range. Particularly, a temperature range of about 110° C. to about 160° C. is useful.

As the heating means, a simple heat plate, iron, heat roller, heat generator utilizing carbon or titanium white, etc., or analogues thereto may be used.

In the present invention, a specific method for forming a color image by heat development comprises transfer of a hydrophilic mobile dye. For this purpose, the heat-developable color photographic material of the present invention is composed of a support having thereon a light-sensitive layer (I) containing at least silver halide, if necessary, an organic silver salt oxidizing agent, a dye releasing redox compound which is also a reducing agent for the organic silver salt oxidizing agent and a binder, and a dye fixing layer (II) capable of receiving the hydrophilic diffusible dye formed in the light-sensitive layer (I).

The above-described light-sensitive layer (I) and the dye fixing layer (II) may be formed on the same support, or they may be formed on different supports, respectively. The dye fixing layer (II) can be stripped off the light-sensitive layer (I). For example, after the heat-developable color photographic material is exposed imagewise to light, it is developed by heating uniformly and thereafter the dye fixing layer (II) or the light-sensitive layer (I) is peeled apart. Also, when a light-sensitive material having the light-sensitive layer coated on a support and a fixing material having the dye fixing layer (II) coated on a support are separately formed, after the light-sensitive material is exposed imagewise to light and uniformly heated, the mobile dye can be transferred on the dye fixing layer (II) by superposing the fixing material on the light-sensitive layer.

Further, there is a method wherein only the light-sensitive layer (I) is exposed imagewise to light and heated uniformly by superposing the dye fixing layer (II) on the light-sensitive layer (I).

The dye fixing layer (II) can contain, for example, a dye mordant in order to fix the dye. In the present invention, various mordants can be used, and polymer mordants are particularly preferred. In addition to the mordants, the dye fixing layer may contain the bases, base precursors and thermal solvents. In particular, it is particularly preferred to incorporate the bases or base precursors into the dye fixing layer (II) in the cases wherein the light-sensitive layer (I) and the dye fixing layer are formed on different supports.

Preferred polymer mordants used in the present invention can be polymers containing secondary and tertiary amino groups, polymers containing nitrogen-containing heterocyclic moieties, polymers having quaternary cation groups thereof, having a molecular weight of from 5,000 to 200,000, and particularly from 10,000 to 50,000.

For example, vinylpyridine polymers and vinylpyridinium cation polymers as disclosed in U.S. Pat. Nos. 2,548,564, 2,484,430, 3,148,061 and 3,756,814, etc., polymers mordants capable of cross-linking with gelatin as disclosed in U.S. Pat. Nos. 3,625,694, 3,859,096 and 4,128,538, British Pat. No. 1,277,453, etc., aqueous sol type mordants as disclosed in U.S. Pat. Nos. 3,958,995, 2,721,852 and 2,798,063, Japanese Patent Application (OPI) Nos. 115228/79, 145529/79 and 126027/79, etc., water-insoluble mordants as disclosed in U.S. Pat. No. 3,898,088, etc., reactive mordants capable of forming cobalent bonds with dyes used as disclosed in U.S. Pat. No. 4,168,976 (Japanese Patent Application (OPI) No. 137333/79), etc., and mordants disclosed in U.S. Pat. Nos. 3,709,690, 3,788,855, 3,642,482, 3,488,706, 3,557,066, 3,271,147 and 3,271,148, Japanese Patent Application (OPI) Nos. 71332/75, 30328/78, 155528/77, 125/78 and 1024/78, etc., can be illustrated.

In addition, mordants disclosed in U.S. Pat. Nos. 2,675,316 and 2,882,156 can be used.

The dye fixing layer (II) can have a white reflective layer. For example, a layer of titanium dioxide dispersed in gelatin can be provided on the mordant layer on a transparent support. The layer of titanium dioxide forms a white opaque layer, by which reflection color images of the transferred color images which can be observed through the transparent support is obtained.

Typical dye fixing material used in the present invention is obtained by mixing the polymer containing ammonium salt groups with gelatin and applying the mixture to a transparent support.

The transfer of dyes from the light-sensitive layer to the dye fixing layer can be carried out using a dye transfer assistant.

In the process in which the dye transfer assistants are supplied from the outside, water and an aqueous solution containing sodium hydroxide, potassium hydroxide or an inorganic alkali metal salt can be used. Further, a solvent having a low boiling point such as methanol, N,N-dimethylformamide, acetone, diisobutyl ketone, etc., and a mixture of such a solvent having a low boiling point with water or an alkaline aqueous solution can be used. The dye transfer assistant may be applied by wetting the dye fixing layer with the transfer assistant.

When the dye transfer assistant is incorporated into the light-sensitive material or the dye fixing material, it is not necessary to supply the transfer assistant from the outside. In this case, the above-described dye transfer assistant may be incorporated into the material in the form of water of crystallization of microcapsules or as a precursor which releases a solvent at a high temperature.

More preferred process is a process wherein a hydrophilic thermal solvent which is solid at a lower temperature and melts at a higher temperature is incorporated into the light-sensitive material or the dye fixing material. The hydrophilic thermal solvent can be incorporated either into any of the light-sensitive material and the dye fixing material or into both of them. Although the solvent can be incorporated into any of the emulsion layer, the intermediate layer, the protective layer and the dye fixing layer, it is preferred to incorporate it into the dye fixing layer and/or adjacent layers thereto.

Examples of the hydrophilic thermal solvents include ureas, pyridines, amides, sulfonamides, imides, alcohols, oximes and other heterocyclic compounds.

The present invention will be explained in greater detail with reference to the following examples, but the present invention should not be construed as being limited thereto. "Percent" in the examples means "percent by weight".

The synthesis examples of dye releasing compounds used in the examples are described in European Patent Application (OPI) No. 76,492.

EXAMPLE 1

40 g of gelatin and 26 g of potassium bromide were dissolved in 3,000 ml of water and the solution was stirred while maintaining the temperature at 50° C. A solution containing 34 g of silver nitrate dissolved in 200 ml of water was added to the above-described solution over a period of 10 minutes. Then, a solution containing 3.3 g of potassium iodide dissolved in 100 ml of water was added for a period of 2 minutes. By controlling the pH of the silver iodobromide emulsion thus prepared precipitate was formed and the excess salts were removed. The pH of the emulsion was then adjusted to 6.0 and 400 g of the silver iodobromide emulsion was obtained.

In the following, a method of preparing a gelatin dispersion of a dye releasing redox compound is disclosed.

A mixture of 5 g of Dye Releasing Redox Compound (I) having a formula described below, 0.5 g of 2-ethylhexyl sodium sulfosuccinate, 5 g of tricresyl phosphate (TCP) and 30 ml of ethyl acetate was heated at about 60° C. to form a uniform solution. The solution was mixed with 100 g of a 10% aqueous solution of gelatin with stirring and then dispersed using a homogenizer at 10,000 rpm for 10 minutes. The dispersion thus prepared is designated a dispersion of dye releasing redox compound.

Dye Releasing Redox Compound (I):

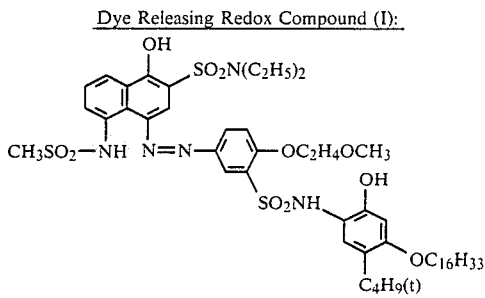

In the following, a method of preparing a light-sensitive coating is described.

| | | |
|---|---|---|
| (a) | The light-sensitive silver iodobromide emulsion described above | 25 g |
| (b) | The dispersion of Dye Releasing Redox Compound (I) | 33 g |
| (c) | A 5% aqueous solution of a compound having the following structure:<br><br>$C_9H_{19}-\phenyl-O(CH_2CH_2O)_{10}-H$ | 10 ml |
| (d) | A 10% aqueous solution of a compound having the following structure:<br>$H_2NSO_2N(CH_3)_2$ | 4 ml |
| (e) | A solution containing 2 g of Base Precursor (3) according to the present invention dissolved in 20 ml of a solvent mixture of water and ethanol (volume ratio of 1:1) | |

The above-described components (a) to (e) were mixed and dissolved by heating. The solution was coated on a polyethylene terephthalate film having a thickness of 180 μm at a wet thickness of 30 μm and dried.

The light-sensitive material thus prepared was exposed imagewise at 2,000 lux for 10 seconds using a tungsten lamp and then uniformly heated for 60 seconds on a heat block which had been heated at 140° C. This is designated Sample A.

Also, Sample B was prepared in the same manner except that component (e) containing the compound according to the present invention was omitted and 20 ml of water was added therefor, and processed in the same manner as described above.

In the following, a method of preparing an image receiving material (this corresponds to a dye fixing material) having an image receiving layer (i.e., dye fixing layer) is described.

10 g of copolymer of methyl acrylate and N,N,N-trimethyl-N-vinylbenzyl ammonium chloride (a mol ratio of methyl acrylate and vinylbenzyl ammonium chloride being 1:1) was dissolved in 200 ml of water and the solution was uniformly mixed with 100 g of a 10% aqueous solution of lime-processed gelatin. The mixture solution was uniformly coated on a paper support laminated with polyethylene containing titanium dioxide dispersed at a wet thickness of 90 μm and dried to prepare an image receiving material.

The image receiving material was soaked in water and superposed on the heated light-sensitive materials described above (Samples A and B) so as to bring into contact with each of the surface layers, and they were heated on a heat block at 80° C. for 6 seconds. The image receiving materials were peeled apart from the light-sensitive materials thereby negative magenta color images were obtained on the image receiving materials. The densities of the negative images were measured using a Macbeth reflective densitometer (RD-519) and the following results were obtained.

| Sample No. | Maximum Density | Minimum Density |
|---|---|---|
| A (Present Invention) | 2.21 | 0.21 |
| B (Comparison) | 0.03 | 0.03 |

From the results shown above, it is apparent that an image having a high color density can be obtained by using the base precursor according to the present invention.

Further, Sample A was preserved at 60° C. for 2 days and then processed in the same manner as described above to obtain the minimum density and the maximum density of 0.25 and 2.24, respectively. From these results it is understood that the sample according to the present invention has a good stability during preservation.

EXAMPLE 2

The same procedure as described in Example 1 was repeated except using the base precursors described below and the results shown below were obtained.

| Sample No. | Base Precursor | Amount Added (g) | Maximum Density |
|---|---|---|---|
| C | (4) | 2.2 | 2.30 |
| D | (8) | 2.2 | 2.19 |
| E | (14) | 2.8 | 2.21 |
| F | (24) | 2.5 | 2.27 |
| G | (27) | 2.0 | 2.31 |
| H | (40) | 2.0 | 2.12 |
| I | (45) | 2.4 | 2.15 |
| J | (46) | 2.2 | 2.33 |

From the results shown above, it is understood that the base precursors according to the present invention have excellent effects.

EXAMPLE 3

Dispersions of dye releasing redox compounds were prepared in the same procedure as described in Example 1 except using the dye releasing redox compounds described below in place of Dye Releasing Redox Compound (10) of Example 1.

Dye Releasing Redox Compound (II) 5 g Dispersion (I)

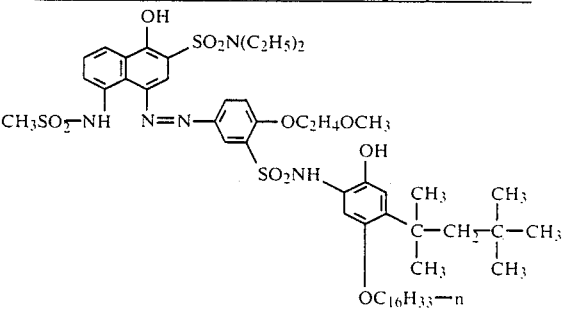

-continued

Dye Releasing Redox Compound (III) 7.5 g Dispersion (II)

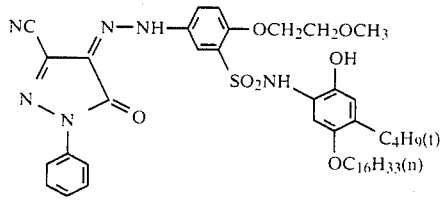

Dye Releasing Redox Compound (IV) 5 g Dispersion (III)

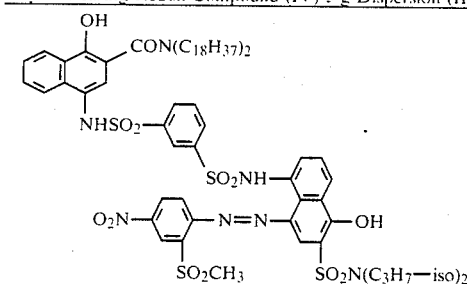

Samples were prepared in the same manner as described in Example 1 and processed in the same manner as in Example 1. The results thus obtained are shown below.

| Dispersion of Dye Releasing Redox Compound | Compound of the Present Invention | Maximum Density | Minimum Density |
|---|---|---|---|
| Dispersion (I) (magenta) | Present | 2.28 | 0.18 |
| | None | 0.03 | 0.03 |
| Dispersion (II) (yellow) | Present | 1.88 | 0.21 |
| | None | 0.03 | 0.03 |
| Dispersion (III) (cyan) | Present | 2.31 | 0.42 |
| | None | 0.20 | 0.05 |

From the results shown above, it is apparent that an image having a high color density can be obtained by using the base precursors according to the present invention.

EXAMPLE 4

In the following, an example in which an organic silver salt oxidizing agent is used is described.

Preparation of Silver Benzotriazole Emulsion 28 g of gelatin and 13.2 g of benzotriazole were dissolved in 3,000 ml of water and the solution was stirred while being maintained at 40° C. A solution containing 17 g of silver nitrate dissolved in 100 ml of water was added to the above-described solution for a period of 2 minutes. By controlling the pH of the silver benzotriazole emulsion thus prepared excess salts were precipitated and removed. The pH of the emulsion was then adjusted to 6.0 and 400 g of the silver benzotriazole emulsion was obtained.

Using the silver benzotriazole emulsion thus prepared, a light-sensitive coating was prepared in the following manner.

| | | |
|---|---|---|
| (a) | A silver iodobromide emulsion (same as described in Example 1) | 20 g |
| (b) | The silver benzotriazole emulsion | 10 g |
| (c) | A dispersion of Dye Releasing Redox Compound (I) | 33 g |

-continued

| | | |
|---|---|---|
| (d) | A 5% aqueous solution of a compound having the following structure: $C_9H_{19}-\phenyl-O+CH_2CH_2O\frac{}{10}-H$ | 10 ml |
| (e) | A 10% aqueous solution of a compound having the following structure: $H_2NSO_2N(CH_3)_2$ | 4 ml |
| (f) | A solution containing 2.5 g of Base Precursor (3) according to the present invention dissolved in 25 ml of a solvent mixture of water and methanol (volume ratio of 1:1) | |

The above-described components (a) to (f) were mixed and then repeated the same procedure as described in Example 1 to prepare samples. The samples were processed in the same manner as described in Example 1 and the results shown below were obtained.

| Sample | Maximum Density | Minimum Density |
|---|---|---|
| With Base Precursor (3) of the Present Invention | 2.40 | 0.23 |
| Without Base Precursor (3) | 0.03 | 0.03 |

From the results shown above, it is apparent that an image having a high color density can be obtained by using the base precursor according to the present invention.

While the invention has been described in detail and with reference to specific embodiments thereof, it will be apparent to one skilled in the art that various changes and modifications can be made therein without departing from the spirit and scope thereof.

What is claimed is:

1. A heat-developable color light-sensitive material comprising a support having thereon at least a light-sensitive silver halide, a binder, a dye releasing redox compound which is capable of reducing the light-sensitive silver halide and is capable of reacting with the light-sensitive silver halide by heating to release a hydrophilic dye and a salt of an alkylcarboxylic acid having a triple bond between the α-position carbon atom and the β-position carbon atom with an organic base as a base precursor.

2. A heat-developable color light-sensitive material as claimed in claim 1, wherein the base precursor is a compound represented by the following general formula (I) or (II):

$$(R-C\equiv C-CO_2H)_x \cdot B \quad (I)$$

$$R+C\equiv C-CO_2H)_2 \cdot B_y \quad (II)$$

wherein R represents a monovalent residue selected from a hydrogen atom, an alkyl group, a substituted alkyl group, a cycloalkyl group, an alkenyl group, an alkynyl group, an aryl group, a substituted aryl group, a heterocyclic group, a substituted heterocyclic group, an aralkyl group, a substituted aralkyl group, an acyl group, an alkoxycarbonyl group, a carbamoyl group, a substituted carbamoyl group, —CO$_2$M (wherein M represents an alkali metal) and —$CO_2H.B$ or a divalent residue selected from an alkylene group, an arylene group and a heterocyclic divalent residue and these groups may be further substituted; B represents an organic base; x represents 1 when B represents a monoacidic base or 2 when B represents a diacidic base; and y represents 1 when B represents a diacidic base or 2 when B represents a monoacidic base.

3. A heat-developable color light-sensitive material as claimed in claim 2, wherein R represents a hydrogen atom, an alkyl group having from 1 to 5 carbon atoms, a substituted alkyl group having from 1 to 5 carbon atoms, a cycloalkyl group having from 5 to 8 carbon atoms, an alkenyl group having from 2 to 5 carbon atoms, an alkynyl group having from 2 to 5 carbon atoms, a phenyl group, a substituted phenyl group, a naphthyl group, a substituted naphthyl group, an anthryl group, a pyridyl group, a substituted pyridyl group, a thienyl group, a substituted thienyl group, a thiazolyl group, a benzoxazolyl group, a benzothiazolyl group, an imidazolyl group, a benzimidazolyl group, a quinolyl group, a furyl group, a pyrrolyl group, an aralkyl group having from 7 to 10 carbon atoms, an acyl group having from 2 to 12 carbon atoms, an alkoxycarbonyl group having from 2 to 9 carbon atoms, a carbamoyl group, a substituted carbamoyl group having from 2 to 9 carbon atoms, —$CO_2Na$, —$CO_2K$, —$CO_2CS$, —$CO_2H.B$ (wherein B represents a base component as described above), a 1,3-phenylene group, a 1,4-phenylene group, a 1,5-naphthylene group, a 2,5-thienylene group or a 9,10-anthrylene group.

4. A heat-developable color light-sensitive material as claimed in claim 2, wherein R represents an alkenyl group, an alkynyl group, a phenyl group, a substituted phenyl group, a naphthyl group, a substituted naphthyl group, an anthryl group, a pyridyl group, a substituted pyridyl group, a thienyl group, a substituted thienyl group, a benzoxazolyl group, a benzothiazolyl group, an acyl group, an alkoxycarbonyl group, a carbamoyl group, a substituted carbamoyl group, —$CO_2M$, —$CO_2H.B$, a phenylene group, a naphthylene group, a thienylene group or an anthrylene group.

5. A heat-developable color light-sensitive material as claimed in claim 2, wherein the base precursor is a compound represented by the following general formula (III) or (IV):

$(Ar-C\equiv C-CO_2H)_x \cdot B$  (III)

$Ar+(C\equiv C-CO_2H)_2 \cdot B_y$  (IV)

wherein Ar represents a phenyl group, a substituted phenyl group, a naphthyl group, a substituted naphthyl group, an anthryl group, a pyridyl group, a substituted pyridyl group, a thienyl group, a substituted thienyl group or a divalent group selected from these groups; and B, x and y each has the same meaning as defined in claim 2.

6. A heat-developable color light-sensitive material as claimed in claim 5, wherein B represents an organic base having a pKa of 9 or more and a boiling point of 100° C. or higher.

7. A heat-developable color light-sensitive material as claimed in claim 5, wherein the organic base represented by B is a guanidine, a cyclic guanidine, an amidine or a cyclic amidine.

8. A heat-developable color light-sensitive material as claimed in claim 1, wherein the base precursor is incorporated in a layer of the material and present in that layer in an amount of 50% by weight or less based on the coated amount of the layer.

9. A heat-developable color light-sensitive material as claimed in claim 8, wherein the base precursor is present in the layer in an amount of 0.01% by weight to 40% by weight based on the coated amount of the layer.

10. A heat-developable color light-sensitive material as claimed in claim 1, wherein the material further contains a dye releasing activator.

11. A heat-developable color light-sensitive material as claimed in claim 1, wherein the material further contains an organic silver salt oxidizing agent.

12. A method of forming a color image comprising imagewise exposing a heat-developable color light-sensitive material comprising a support having thereon at least a light-sensitive silver halide, a binder, a dye releasing redox compound which is capable of reducing the light-sensitive silver halide and is capable of reacting with the light-sensitive silver halide by heating to release a hydrophilic dye and a salt of an alkylcarboxylic acid having a triple bond between the α-position carbon atom and the β-position carbon atom with an organic base and heating the exposed light-sensitive material under a condition substantially free from water to imagewise release a mobile dye.

13. A method of forming a color image as claimed in claim 12, wherein the heating of the light-sensitive material is carried out at a temperature of at least 80° C.

14. A method of forming a color image as claimed in claim 12, wherein the mobile dye released is then transferred into a dye fixing layer.

* * * * *